United States Patent
Tian et al.

(10) Patent No.: US 6,727,359 B2
(45) Date of Patent: Apr. 27, 2004

(54) COMPOSITION COMPRISING 6-METHYL-3, 4DIHYDRO-1,2,3-OXATHIAZIN-4-ONE-2,2-DIOXIDE, ITS SALTS, PREPARATION THEREOF AND USES THEREFOR

(75) Inventors: Nianshou Tian, Beijing (CN); Haiming Liu, Beijing (CN)

(73) Assignee: BDL Corporation, Forest Hills, NY (US)

( * ) Notice: Subject to any disclaimer, the term of this patent is extended or adjusted under 35 U.S.C. 154(b) by 0 days.

(21) Appl. No.: 10/206,421

(22) Filed: Jul. 25, 2002

(65) Prior Publication Data

US 2003/0065172 A1 Apr. 3, 2003

(30) Foreign Application Priority Data

Jul. 25, 2001 (CN) ........................................ 01120592 A

(51) Int. Cl.⁷ .............................................. C07D 29/06
(52) U.S. Cl. ........................................................... 544/2
(58) Field of Search ............................................... 544/2

(56) References Cited

U.S. PATENT DOCUMENTS

| 4,394,153 A | 7/1983 | Reap ............................. 71/92 |
| 5,011,982 A | 4/1991 | Clauss et al. ................. 562/38 |
| 5,103,046 A | 4/1992 | Clauss et al. ................. 562/40 |

FOREIGN PATENT DOCUMENTS

| CN | 931021898 | 3/1993 |
| DE | 2219923 | 4/1972 |

OTHER PUBLICATIONS

Spillane, W.J. and Burke, P.O., Acylation and Sulfonylation of Sulfamate Esters; Synthesis of an Acesulfam K Precursor. Synthesis, 12:1021–23 (1986) [Exhibit 8].

Hedayatullah, M. and Hugueny, J. C., An Improved General Procedure for the Synthesis of Aryloxysulfonyl Azides. Synthetic Communications, 11(8) :643–46 (1981) [Exhibit 9].

Hedayatullah, M. and Guy, A., A Convenient Synthesis of Aryl Sulfamates. Synthesis, 5:357 (1978) [Exhibit 10].

Lohaus, G., Darstellung und Umsetzungen von Aryloxysulfonylisocyanaten. Chem. Ber., 105:2791–99 (1972) [Exhibit 11].

Shuman, D. et al., The Synthesis of Nucleoside Sulfamates Related to Nucleocidin. J. Am. Chem. Soc., 92(11):3434–40 (1970) [Exhibit 12].

Buncel, E. et al., Bond Scission in Sulfur Compounds. VIII. Reaction of Aryl Chlorosulfates with Anionic Nucleophiles. J. Am. Chem. Soc., 95(18):5964–67 (1973) [Exhibit 13].

Stiles, A.B. and Koch, T.A., Catalysts for Synthesis Gas Processing, in Catalyst Manufacture. Macrel Dekker, N.Y. (1995), pp. 145–154 [Exhibit 14].

Starks, C.M. and Liotta, C.L., Phase–Transfer Catalysts. Chapman & Hall, N.Y. (1993), pp. 145–160 [Exhibit 15].

*Primary Examiner*—John M. Ford
(74) *Attorney, Agent, or Firm*—Albert Wai-Kit Chan; Mark Elkins

(57) ABSTRACT

Acesulfame-K is a widely used sweetener in food and beverage. It is prepared by using the substituted sodium phenoxide or substituted phenol as the starting substance to synthesize the following three intermediates: a substituted phenoxide sulfonylchloride(I), a substituted phenoxide sulfonylamide(II) and an acetoacetamide-N-sulfonyl-substituted phenoxide(III). Particularly, II was prepared by using the liquid or gaseous ammonia to react with I under the action of some catalysts in a reaction column. III was prepared by using II to react with diketene. Acesulfame-K was prepared by ring-closure in III with methanol solution of KOH or $K_2CO_3$.

24 Claims, No Drawings

COMPOSITION COMPRISING 6-METHYL-3, 4DIHYDRO-1,2,3-OXATHIAZIN-4-ONE-2,2-DIOXIDE, ITS SALTS, PREPARATION THEREOF AND USES THEREFOR

Throughout this application, various references are referred to within parenthesis. Disclosures of these publications in their entireties are hereby incorporated by reference into this application to more fully describe the state of the art to which this invention pertains.

FIELD OF INVENTION

This invention relates to a process for preparing a chemical substance. 6-Methyl-3,4-dihydro-1,2,3-Oxathiazin-4-one dioxide is the compound expressing as the following molecular formula (hereinafter Acesulfame)

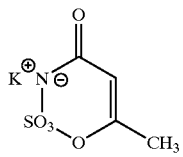

Because of the acidic hydrogen on the nitrogen atom, the compound is able to form salts (with bases). The non-toxic salts, for example the sodium, Na, potassium, K and calcium, Ca salt, can, because of their sweet taste, be used as sweeteners in the foodstuffs sector, the K salt ("Acesulfame K") being of particular importance.

BACKGROUND OF THE INVENTION

Acesulfame-K (AK) is a kind of synthesized high-degree and healthier sweetener. It tastes like cane sugar but 200 times sweeter than the latter. Because of the remarkable characters, such as strong sweet, good stability, fresh taste, fine flavor, no bitter metallic and chemical feeling, cheaper price, safety and no side effect after a large number of toxic tests, AK is a favorite in the international market. Since 1980's, in many developed countries such as America and Europe, Ak. has widely been used in the production of foods, medicine and cosmetics. These years, with AK more widely being used in beverage and medicine, AK is widely accepted by more and more clients as an important new kind of healthier sweetener.

A number of different processes are known for the preparation of AK and its non-toxic salts. Forty-five patents of Acesulfame filed in five countries were reviewed.

See the following list.

| BP | CN | DE | EP | US | Total |
|----|----|----|----|----|-------|
| 4  | 14 | 10 | 3  | 14 | 45    |

The description of the processes for preparing Acesulfame in these patents may be summarized below:

(1) Using fluoro or chlorosulfonyl isocyanate ($XSO_2NCO$ with x=Cl or F) reacted with tertiary-butylacetoacetate. In the processes, the intermediate fluoro or chlorosulfonyl isocyanate was produced necessarily to use potassium cyanate, that is a very poisonous substance. It is very easy to cause a person working at the post to be seriously hurt, or even death if the safety measures were not perfectly observed. Therefore, this process is not suitable for large industrial production. Additionally, this reaction needs to carry out at lower temperature, thus it is necessary to take much energy that making the productive costs increase. As mentioned above, the process is disuse in industry at present.

(2) Reactions of sulfurylfluoride and acetoacetamide.

(3) Reactions of diketene and sulfamoyl fluoride ($H_2NSO_2F$). In methods (2) and (3) it is difficult to produce sulfurylfluoride and sulfamoyl fluoride in industry. It is necessary to use hydrofluoride for producing the above two substances. A common work lacks perfect safe guard to protect workers against the health hazard of HF. Therefore the above two methods aren't suitable to produce Acesulfame in industry.

(4) The reaction of ring closure of acetoacetamide-N-sulfonic acid with sulfur trioxide at lower temperature was applied to prepare Acesulfame.

But in this process the quantity of sulfur trioxide is as much as four to five times of acetoacetamide-N-sulfonic acid while produced 1 ton of Acesulfame therefore 2 tons of waste sulfuric acid was given here, it was very difficult for manufacturers to treat so large amount of waste acid. The reaction of ring closure must be carried out at lower temperature so it needs to take a lot of energy to reduce the temp of reactants. Additionally, sulfur trioxide is very easy to polymerize turning into various forms of Polymers. At room temperature these polymers are in solid form. Thus the concentration of Sulfur trioxide is difficult to control during the period of practical operation. As a result it leads to the unsteady yield of products desired. Sulfurtrioxide is also a strong oxidant as it absorbed water to turn into sulfuric acid which has strong corrosive action to iron or steel equipments. Judging from this the process isn't a good way for preparing Acesulfame.

In CN patent No.1092066 the synthetic methods of Acesulfame are shown in the following reaction equations:

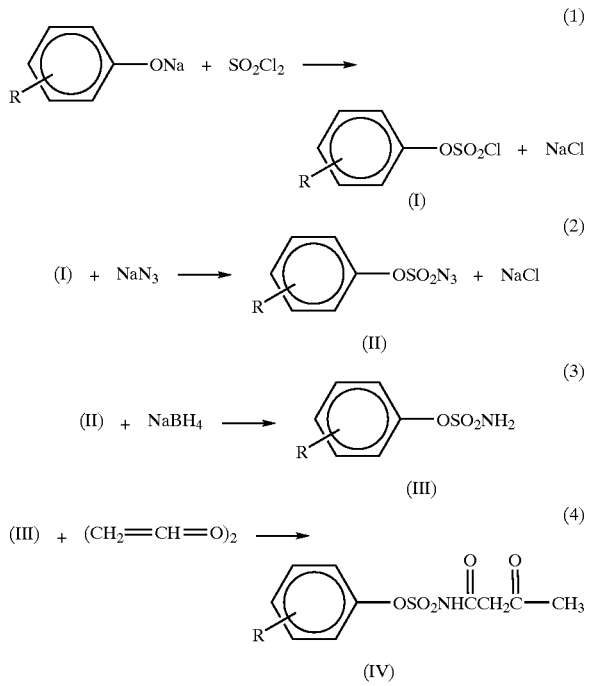

(IV) + 2KOH →

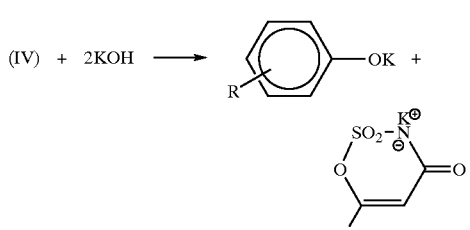

+ 2H₂O

Acesulfame-K

In the above equation (2) sodium azide was used to react with p-chlorophenoxide sulfonylchloride for preparing p-chlorophenoxide sulfonylazide. After completion of the reaction, solvent was required to distill off, but at this moment attention must be paid to the temperature of distillation. If the distilling temperature exceeded 25° C., it was surely to lead to a terrible explosion. It is a dangerous factor that exists in this synthetic process.

In the above equation (3) p-chlorophenoxide sulfonylazide was reduced to amino-group with sodium tetrahydroborate (NaBH₄), but this reductive agent sparingly dissolves in tetrahydrofuran. Under this condition the reductive time, was very long that caused the reductive effect bad, therefore it made the yield of the product unsteady according to the above mention in CN patent 1092066. The two defects of the synthetic processes of Acesulfame must be modified to the reaction equations (2) and (3). Therefore, we have done many experiments in order to find a good way to replace the above reaction equations (2) and (3).

This object has been achieved according to the invention by a modification of the process of China patent publication No.1092066.

Our group found an advertisement in a German Journal in which Acesulfame-K was described in 1983. In 1992, our group had synthesized Acesulfame-K. The result led to filing a patent application in China in 1992.

However, the above synthetic method of Acesulfame-K was not satisfactory. Below describes an improved method for Acesulfame-K.

Acesulfame-K's patents:

| No. | Country | Patent No. |
|---|---|---|
| 1 | B.P | 1326861 |
| 2 | B.P | 1340911 |
| 3 | B.P | 1452099 |
| 4 | B.P | 1456689 |
| 1 | DE | 2453063 A₁ |
| 2 | DE | 3410233 A₁ |
| 3 | DE | 3410439 A₁ |
| 4 | DE | 3410440 A₁ |
| 5 | DE | 3429039 A₁ |
| 6 | DE | 3531357 A |
| 7 | DE | 3531358 A₁ |
| 8 | DE | 3527070 A₁ |
| 9 | DE | 3531357 A |
| 10 | DE | 19859663 A₁ |
| 1 | EP | 0217024 |
| 2 | EP | 0218076 |
| 3 | EP | 2327804 |
| 1 | USP | 3689485 |
| 2 | USP | 3689486 |
| 3 | USP | 3917589 |
| 4 | USP | 3926981 |
| 5 | USP | 3926976 |
| 6 | U.S.P | 3993689 |
| 7 | U.S.P | 4052453 |
| 8 | U.S.P | 4563521 |
| 9 | U.S.P | 4607100 |
| 10 | U.S.P | 5103046 |
| 11 | U.S.P | 5011982 |
| 12 | U.S.P | 1326861 |
| 13 | U.S.P | 1452099 |
| 14 | U.S.P | 1456689 |
| 1 | CN | 85104257 |
| 2 | CN | 85104277 |
| 3 | CN | 85106284 |
| 4 | CN | 86105339 |
| 5 | CN | 86105506 |
| 6 | CN | 86105877 |
| 7 | CN | 90108023 |
| 8 | CN | 90107999 |
| 9 | CN | 93102657 |
| 10 | CN | 85104278 |
| 11 | CN | 1092066 A |
| 12 | CN | 1257865 |
| 13 | CN | 1154965 |
| 14 | CN | 1336363 |
| 15 | CN | 8610550 |

Some main differences in preparing Acesulfame-K between German, US patents and our invention are:

Synthetic schemes are different:
1 USP, DE:

(1) U.S. Pat. No. 3993689 (Nov. 23, 1976)

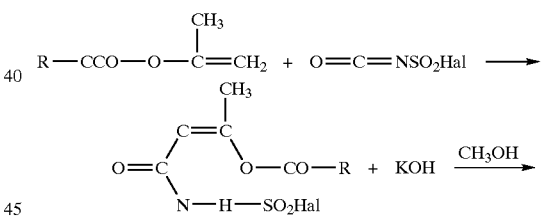

(2) U.S. Pat. No. 4,052,453 (Oct. 4, 1977)
U.S. Pat. No. 3,969,347 (Jul. 13, 1976)

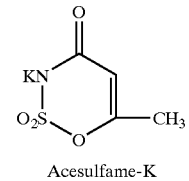

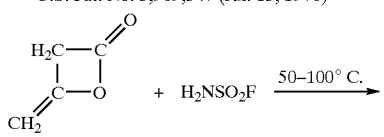

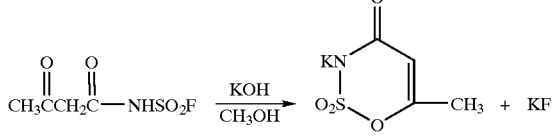

(3) U.S. Pat. No. 5,011,982 (Apr. 30, 1991),
U.S. Pat. No. 5,103,046 (Apr. 7, 1992)

-continued

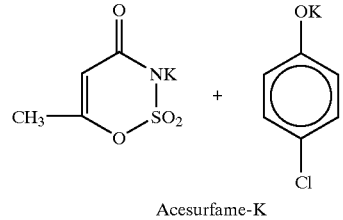

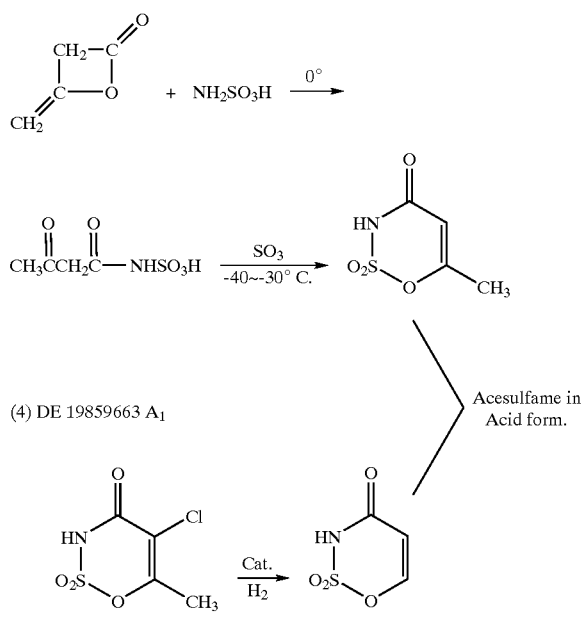

(4) DE 19859663 A₁

2 Our Invention:

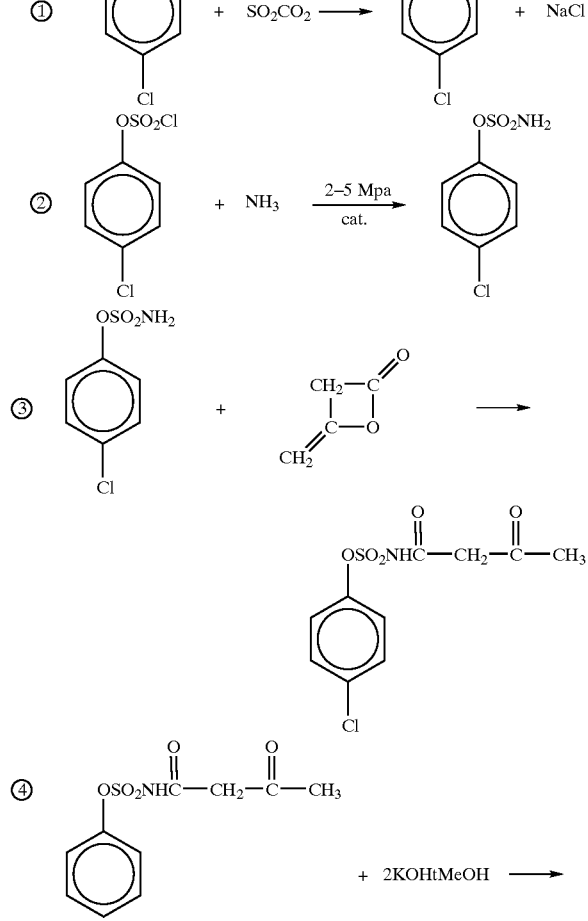

-continued

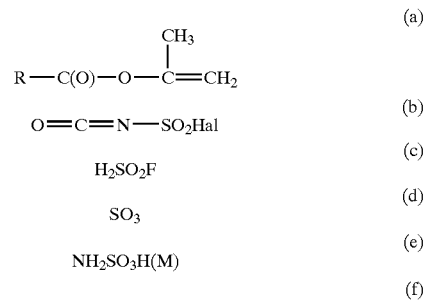

Acesurfame-K

B, Raw materials used as synthetic components are different between USP, DE patent and Our Invention:

In USP:

(a)

$$R—C(O)—O—\underset{CH_3}{\underset{|}{C}}=CH_2$$

(b)

$$O=C=N—SO_2Hal$$

(c)

$$H_2SO_2F$$

(d)

$$SO_3$$

(e)

$$NH_2SO_3H(M)$$

(f)

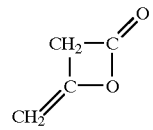

These substances must be manufactured by producer. One can't easily obtain them from market. If one needs to produce (b), (c), NaCN, HF, two poisonous substances must be used in producing processes.

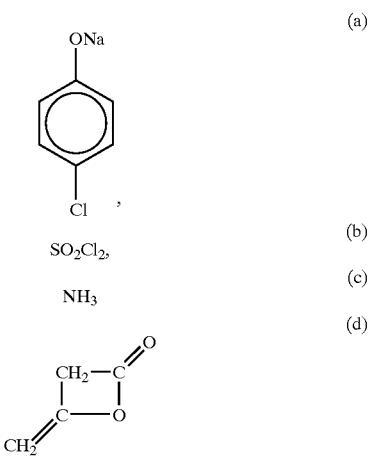

In Our invention:

These substances are very easy to be bought from market.

C, The waste substances occurred in our synthetic ways are less than that of US patent in preparing Acesulfame-K.

In our invention:

All solvents can be recovered from each step, and be reused in precedent steps. By product, Potassium Chlorophenoxide can be easily separated from Acesulfame-k and be reused in the first step.

In US Patent:

The waste substances produced in synthetic Acesulfame-k are more than ours. Such as $SO_3 + H_2O \rightarrow H_2SO_4$ in U.S. Pat.

Nos. 5,011,982 and 5,103,046, those amounts are large, and can't be reusable. Because it contained a lot of impurities and its color is dark brown. So it becomes a big problem to process for producers.

SUMMARY OF THE INVENTION

This invention provides a method for preparing Acesulfame comprising steps of: (a) using the substituted sodium phenoxide or the substituted phenol reacted with sulfonyl chloride in a suitable inert solvent under catalysis to produce substituted phenoxide sulfonylchloride, Compound I; (b) reacting Compound I with ammonia under catalysts to produce substituted phenoxide sulfonyl-amide, Compound II; (c) reacting Compound II with diketene in an organic solvent under amine catalysts to produce acetoacetamide-N-sulfonyl-substituted phenoxide, Compound III; (d) dissolving Compound III in lower alcohol and addition of alkali metal hydroxide or carbonate so that cyclyzation of Compound III will occur to produce acesulfame; and (e) harvesting the produced Acesulfame.

DETAILED DESCRIPTION OF THE INVENTION

This invention provides a method for preparing Acesulfame comprising steps of (a) using the substituted sodium phenoxide or the substituted phenol reacted with sulfonyl chloride in a suitable inert advent under catalysis to produce substituted phenoxide sulfonylchloride, Compound I; (b) reacting Compound I with ammonia under catalysts to produce substituted phenoxide sulfonyl-amide, Compound II, (c) reacting Compound II with diketene in an organic solvent under amine catalyses to produce acetoacetamide-N-sulfonyl-substituted phenoxide. Compound III; (d) dissolving Compound III in lower alcohol and addition of alkali metal hydroxide or carbonate so that cyclyzation of Compound III will occur to produce acesulfame; and (e) harvesting the produced Acesulfame.

In an embodiment of step (a) the inert solvent includes a group of alkyaryl hydrocarbons, halohydrocarbons.

In a further embodiment, the reaction comprises some cosolvents.

In another embodiment of step (a), the solvent includes but is not limited to methylene chloride, 1,1-dichloro ethane, and 1,2-dichloro ethane.

In a separate embodiment, the catalysts of step (a) includes alkyl of alkoxy ammoniumhalides.

In another embodiment of step (a) the temperature is at approximately −10 to +20° C., In another embodiment of step (a), the reaction is stirring continuously.

In a separate embodiment of step (a), the pressure of reaction inside the column is between 2 to 10 Mpa.

The catalysts include but are not limited to following compounds: $SiO_2$—$Al_2O_3$, NiO, $Cu_2O$, $TiO_2$, $ThO_2$ and $Cu(OH)NH_4CrOH$, $NI_6Al_2C(OH)_{16}CO_3 \cdot 4H_2O$, $Ni/Al_2O_3$—$NiO/SiO_2$, or other metals including: pd, pt, Ni.

In an embodiment of step (C), organic solvent includes benzenes, halohydrocarbon, ether, tetrahydrofuran, and acetonitrile.

In a separate embodiment of step (c), the temperature is approximately −5° C. to +10° C.

The amine catalysts of step (c) included but are not limited to trimethylamine triethylamine, tri-n-propylamine, triisopropylamine, tri-n-butylamine, and triethylamine.

In an embodiment of step (a) and step (b), solvents used include the following organic solvent: benzene, methylenechloride, monochloromethane, chloroform, ethylidene chloride, 1,2-dichloroethane, tetrahydrofurane toluene, and o-,m-,p-three kinds of xylene.

This invention encompasses the substituted radical R in its molecular formula, represented H—, 2-$CH_3$—, 2,6-di-$CH_3$—, 2-Cl, 4-Cl, 2-$NH_2$—, catalyst used here was selected from a group consisting of alkyl-or alkoxy-onium salts, tribenzyl ethyl ammoniumchloride, tribenzyl ammonium bromide, tetra-n-butylammonium bromide, tetra-1-butyl ammonium chloride and tetra-1-butylammonium bromide.

In an embodiment of step (c), the solvent includes the following solvent: benzene, methylenechloride, monochloromethane, chloroform, carbontetrachloride, ethylchloride, ethylidenechloride, dichloroethane, diethylether, methyl ethyl ether and tetrahydrofuran. The amine catalysts are tertiary amines in which each N atom has up to 20, or only up to 10 carbon atoms selected as catalyst. In a further embodiment, the amines catalysts is trimethylamine, triethylamine, tri-n-propylamine, triisopropylamine, tri-n-butylamine, triisobutylamine, N,N-dimethylamine etc. A particular preferred is the triethylamine. The reaction time can vary within wide limits in general, i.e. between 1.5 to 12 hours, Compound III can be recrystallized from a suitable solvent such as acetone, methylacetate or ethanol.

In an embodiment of step (d), the hydroxide or carbonate of alkali metals is selected from NaOH, KOH, $Na_2CO_3$, $K_2CO_3$, K alcoholate, ROK where R=$CH_3$—, $CH_3CH_2$—, $CH_3CH_2CH_2$—.

In a separate embodiment of step (d), the alcoholic solvent is a lower alkylalcohol. In a further embodiment, the alcohol solvent is methanol, ethanol and propanol.

In a still further embodiment of step (d), the temperature in the reaction of ring closure at approximately 10° C. to 30° C. In another embodiment of step (d), the pH value at the end of the ring closure reaction was 8 to 12.

This invention also provides acesulfame produced by the above method and compositions comprising the produced acesulfame. Acesulfame-K, an intense sweetener being wide used in food and beverage now, may be prepared by: a) using the substituted sodium phenoxide or substituted phenol as the starting substance synthesized the following three intermediates; The substituted phenoxide sulfonylchloride(I), The substituted phenoxide sulfonylamide(II), The acetoacetamide-N-sulfonyl-substituted phenoxide(III); b) particularly, the (II) was prepared by using the liquid or gaseous ammonia to react with (I) under the action of some catalysts in a reaction column. The (III) was prepared by using the (II) to react with diketene; c) Acesulfame-K was prepared by ring-closure in the molecule of (III) with methanol solution of KOH or $K_2CO_3$.

Thus, the invention relates to a process for the preparation of Acesulfame and its non-toxic salts is described as follows:

Step (1) Preparing the substituted phenoxide sulfonylchloride [hereafter called Compound I].

Using the substituted sodium phenoxide or the substituted phenol that reacted with sulfonyl chloride, under the catalytic action to produce Compound (I). The reaction temperature was at −10° C. to approximately −20° C.

Alkyl-or alkoxyammonium halide was used as catalyst.

Their reaction was carried out in the solvent of chlorohydrocarbon, alkyl-arylhydrocarbon, if necessary, added some cosolvent to above solvents for raising their solubility, such as polyethyleneglycol (PEG) is normally used, the molecule weight of PEG was selected between 400 to 600.

Step (2) preparing the substituted phenoxide sulfonylamide [hereafter called Compound II]

Let the Compound I dissolved in halohydrocarbon solvent, and then being pumped the solution into the reaction column. Cooling the solution inside the column to the temperature at −5° C.~+30° C. The pressure in the column was nearly regulated in 2~10 Mpa by sending liquid or gaseous ammonia into the column for going on the ammonification reaction with Compound I. Under the actions of some catalysts which had been put into the column before the process begun. After the reaction, obtained the intermediate, Compound II.

Step (3) Preparing acetoacetamide-N-sulfonyl substituted phenoxide [hereafter called Compound III].

Using the above Compound II reacted with diketene in a suitable inert organic solvent in which appropriate amount of a tertiary amine was used as catalyst to produce Compound III.

An inert organic solvent used here was selected from the following organic solvents, such as benzene, halogenated aliphatic hydrocarbons, preferably those having up to 4 carbon atoms, for example, methylene chloride, chloroform, 1,2-dichloroethane, trichloroethylene, tetrachloroethylene, aliphatic ethers, such as furamidine, dioxane etc. aliphatic nitrites, preferably acetontrile. The reaction temperature was at −5° C.~+5° C.

Step (4) Preparing Acesulfame-K.

At room temperature let the Compound III dissolve in the lower alcohol. Under continuously stirring, the alcoholic solution of alkali metal hydroxide or carbonate van adding dropwise to the alcoholic solution of Compound III. Under this condition the Compound III occurred a cyclization reaction in its molecule and the final Compound. Acesulfame-K, was precipitated from the alcoholic solution; at PR 8-12.

In step (1) the substituted R in the molecule of sodium Phenoxide or phenol may be H, -2—CH3-, 2,6-dimethyl-, 2-chloro-, 4-chloro, 2-amino.

Catalyst used in step (1) was selected from alkyl-or alkoxyloniumshalide such as benzyl triethylammoniumchloride, benzyl triethylammoniumbromide, tetra-n-butylammoniumbromide tetra-i-butylammoniumchloride. Suitable inert organic solvent used in step (1) was Selected from chlorohydrocarbon alkyl, arlhydrocarbon such as benzene, dichloromethane, chloroform, 1, 1-dichloroethane, 1,2-dichloroethane, 1,2-dichloroethane toluene, m-,o-,p- three kind, of xylene, if necessary added some cosolvents to anyone of the above solvents such as polyethyleneglycol (PEG M.W 400~600). etc.

In step (2) ammonia used here was liquid or gaseous state, catalysts used here were selected from the following substances. Hexamethyleneamine, $SiO_2$—$Al_2O_3$, $TiO_2$, $ThO_2$, $NiO/Al_2O_3$, cuprous oxide, Cupric oxide, $Cu(OH)_2$, $NH_4CrOH$, $Ni_6Al_2(OH)$ $CO_3.4H_2O$, Pd, Pt, Ni, Rh and the mixtures oxides of various metals.

Solvent used here was selected form benzene, methylenechloride, chloroform. 1,1-dichloroethane, 1,2-dichloroethane, toluene, O—, m, p-three kinds of xylene, tetrahydrofuran etc.

In step (3) the solvent used here was selected from Benzene, monochloromethane, methylenechloride, chloroform, carbontetrachloride, monochloroethane, 1,2-dichloroethane, 1,1-dichloroethane, ether methylethylether, acetone, tetrahydrofuran, acetonitrile, etc.

Akylamine used here was selected from diethylamine triethylamine, tri-n-propylamine, triisopropylamine, tri-n-butylamine, tricyclohexylamine, N,N-dimethylaniline, benzyl dimethylamine, pyridine substituted pyridines. A particularly preferred amine is triethylamine.

In step (4) the hydroxide or carbonate of alkali metals used here was selected from NaOH, $Na_2CO_3$, KOH, $K_2CO_3$, preferably using a potassium base, for examples, KOH, $K_2CO_3$, K alcoholate etc.

Alcoholic solvent used in step (4) was selected from alkyl alcohol having 1~3 atoms of carbon such as methanol, ethanol, propanol etc. A particularly preferred alcohol is methanol.

The temperature for cyclization reaction was controlled at 10° C.~30° C., PH value was 8~12.

This invention improves the reaction in step (2) of CN patent, No.1092066. Liquid or gaseous ammonia was used instead of sodium azide. Under the action of some catalysts at a certain pressures and temperature the reaction would be taking place. Catalyst such as $SiO_2$, $Al_2O_3$ or others was put into the reaction column, and then the methylene chloride solution of Compound I was pumped into the same column. Liquid ammonia was let to enter into the same column till it cooled at the temp 0° C.~15° C. The speed of liquid or gaseous ammonia was adjusted to allow the pressure meter fitted on the top of the column indicated 2–10 Mpa. The aminolysis reaction at this pressures and temperature was carrying on to 3 h. If the pressure dropped during the reaction period, at this moment the speed of liquid or gaseous ammonia entering the column should be adjusted till the pressure was steadily. After the reaction having proceeded for 3 h, sampling the reaction liquid to be tested. If the content of desired product reached 80~90%, It indicated that the reaction was completed.

Let the reaction solution flow into a distillatory, and under reduced pressure for distilling the residuce ammonia and methylene chloride, thus obtained p-chlorophenoxide sulfonylamide.

Some Advantages of this Invention are Summed up as Follows:

Technical process is simple, reaction time is short and the industrial wastes are treated easily. The yields of three intermediates and finished substance are higher than other methods. Therefore the defects in CN patent, 1092066 (Application No.93102189) have been improved.

EXAMPLES

Synthesis of Acesuflame-K (1) Preparing the substituted phenoxide sulfonylchloride, [hereafter called Compound (I)]

Using the substituted sodium phenoxide or the substituted phenol reacted with sulfonylchloride to produce Compound (I). The reaction temperature was at −10° C.~20° C. Alkyl or alkoxy ammonium halide was used as catalyst. This reaction carried on in the organic cosolvent of chlorohydrocarbon or alkyl, arylhydrocarbon, sometimes adopting polyethylene glycol (PEG) used as solvent.

(1) Preparing the substituted phenoxide sulfonylamide [hereafter called Compound (II)]

Let compound (I) dissolve in halohydrocarbon and then pumped the solution into the reaction column. Cooling the solution inside the column to the reaction temperature −5° C.~+20° C. The pressure inside the column was controlled in 2~10 Mpa as liquid or gaseous ammonia being sent into the column wherein it reacted with Compound (I) Under the action of catalysts.

(2) Preparing 4-chlorophenoxide N-acetoacetylsulfamate [hereafter called Compound (III)]

Using Compound (II) reacted with diketene in the organic solvent which was selected from benzene, haloalkyl hydrocarbon, ether, acetone, tetrafuran, and acetonitrile etc. A particularly preferred solvent is methylene chloride.

The reaction temperature was at −5° C.~+5° C. The tertiary alkylamine or arylamine was used as catalyst in the reaction.

(3) Preparing Acesulfame-K

At room temperature let Compound (III) dissolve in lower alcohol, under continuously stirring, the alcoholic solution of alkali metal hydroxide or carbonate wan added dropwise to the above solution of Compound (III), under this condition the Compound (III) carried out cyclization in its molecule, potassium hydroxide should be used in an at least stoichiometric amount according to the aforesaid reaction equation, i.e. at least 2 moles per mole. Compound (In) or in a slight excess of up to 10%, preferably up to 5%, in order to obtain as complete as possible for a reaction. After the reaction, crystal of Acesulfame-K was precipitated from the alcoholic solution.

In step (1) the substitute redical R in the molecule of sodium phenoxide or phenol may be H—, 2-cH$_3$—, 2,6-dimethyl-, 2-chloro-, 4-chloro-, 2-amino-, 6-amino-.

Catalyst used in step (1) was selected from alkyl or alkoxyloniums halide such as benzyltriethylammoniumchloride, Benzyltriethylammoniumbromide. Tetra-n-butyl ammonium bromide, tetra-1-butyl ammoniumchloride. The amount of catalysis normally up to shout 0.1 mole per mole of substituted sodium phenoxide or substituted phenol, large amounts ire possible, but entail any advantages hardly.

The organic solvent used is step (1) was selected from benzene, various kinds of xylenes, monochloromethane, methylenechloride, 1,1-dichloroethane 1,2-dichloroethane, or if necessary polyethylene glycol used as cosolvent was mixed with anyone of the above mentioned solvent.

Ammonia used in step (2) was either in liquid or in gaseous state, particularly preferred ammonia is in liquid state.

The catalysts used in step (2) were selected from hexamethyleneamine, $SiO_2$—$Al_2O_3$, $TiO_2$, $TiO_2$, $ThO_2$, $NiO/Al_2O_3$, $Cu_2O$, $Cu(OH)NH_4CrOH$, $Ni_6Al2(OH)_6CO_3$, Pd, Pt, Ni, Rh and the mixture of various metal oxides.

The organic solvent used here was selected from benzene, methylene chloride, chloroform, 1,1-dichloroethane, 1,2-dichloroethane, ether toluene, m-,o-,p-, three kinds of xylene, tetrafurane etc.

In step (3) the organic solvent used was selected from benzene, monochloromethane, methylenechloride, 1,1-dichloroethane, 1,2-dichloroethane, ether methyl ethylether, acetone tetrahydrofuran, acetonitrile.

The solvent can be used either alone or in mixture, the ratio of the amount of the reaction starting materials to the solvent can vary within wide limits; the weight ratio is about 1:(2–5). However, other ratios are also possible.

In principle, the amine catalysts which can be used are all amines, the use of which as catalyst for addition reaction of diketene is known.

These are mainly tertiary amines having nucleophilic characteristics. Those, which are preferred in the present cases are tertiary amine in which each N atom has up to 10 carbon atoms. The following tertiary amines may be mentioned as examples:

Trimethylamine, triethylamine, tri-n-propylamine, triisopropylamine, tri-n-butylamine, triisobutylamine, tricyclohexylamine, ethyldiisopropylamine, N,N-diethylamine, benzyldimethylamine.

A particularly preferred amine is triethylamine.

In principle, reaction step (3) of the process according to the invention also takes place without catalyst; however, the catalyst acts to accelerate the reaction and is thus advantageous. In general, the reaction temperature is selected to be in a range between about −20 and +20° C., preferably between −5° C. and +5+ C.

The reaction is normally carried out under atmospheric pressure. The reaction time can vary within wide limits; in general, it is between 1.5 and 12 hours. After the reaction is complete for the isolation of the reaction product, the solvent is removed by distillation, and the residue mainly Compound (III) is recrystallized from a suitable solvent such as acetone, methyl acecate or ethanol. The yield is about 85 to 90% of theory.

In step (4) Alkali metal hydroxides used were selected from NaOH, KOH, or alkali metal carbonates $Na_2CO_3$ and $K_2CO_3$.

Alcoholic solvents used here were selected from lower alkyl alcohol having 1~3 carbon atoms, such as methanol, ethanol, propanol etc, With increasing water content in the methanol the solubility of Acesulfame-K increase, therefore, with consideration of the water possibly formed in the reaction, the proportion of water in the reaction mixture should not exceed 50% by weight, preferably 20% by weight calculated on the methanol used. The temperature for ring closure reaction was at approximately 10~30° C. The range of PH values was between 8~12.

The following experiments are being used to illustrate the invention.

Experiment 1
Preparing p-chlorophenoxidesulfonyl chloride [hereafter called Compound (I)]

| Exp. No. | Starting Materials | | | solvents | cosolvents | Temp (° C.) | Processing time | Yield of Compd(I) | Rate of yield (%) |
| --- | --- | --- | --- | --- | --- | --- | --- | --- | --- |
| | Sodium Para-chlorophenoxide | Sulfonyl chloride | catalysts | | | | | | |
| 1 | 15.0 g(0.1 mol) | 13.5 g(0.1 mol) | 2.0 g of TEAC(1) | Benzene | — | −3~+3 | 3 h | 14.5 g | 63.8 |
| 2 | 30.0 g(0.2 mol) | 28.0 g(0.2 mol) | 3.0 g of TEAB(2) | 1,1-dichloro-ethane | — | 0~+3 | 3 h | 12.5 g | 51 |
| 3 | 15.0 g(0.1 mol) | 14.0 g(0.1 mol) | 2.0 g of BTEAC(3) | Methylene Chloride | 10 g of PEG(400) | 0 | 3 h | 20.1 g | 89 |
| 4 | 15.0 g(0.1 mol) | 14.0 g(0.1 mol) | 2.0 g of TEAC | Methylene Chloride | 10 g of PEG(400) | 0 | 3 h | 20.3 g | 90 |

Note:
(1)TEAC: triethylammonium Chloride
(2)TEAB: triethylammonium Bromide
(3)BTEAB: Benzyl triethylammonium bromide
(4)PEG: Polyethylene glycol (M.W. 400~600)
*Operating processes as the following Exp(5) mentioned
*The vessels used in Exp(1)~(4) were 500 ml of two necks flask and magnetic stirrer In 100 L reactor, 60 L of dried methylene chloride, 9 Kg (60 mol) sodium p-chlorophenoxide and suitable amount of catalyst (the amount of catalyst is normally up to about 0.1 mole of beyltriethyl ammonium chloride calculated based on per mole of sodium p-chlorophenoxide), were added and the reaction was continuously stirred. As the temperature in the reactor dropped to 0° C., began to add dropwise 8.1 Kg (60 mol) of sulfonyl chloride dissolved in 3000 L methylenechloride. This procedure was completed within 1.5 h. Afterwards the temperature of reaction solution was raised to room temperature. The reaction was continuously stirring for 2 h at the temperature. After completion of the reaction, the solid substances deposited in the reaction solution should be filtered off with suction. Distilled off the solvent from the filtrate, thus obtained about 14.2 Kg of p-chlorophenoxide sulfonylchloride (I). The yield of Compound (I) was about 90%. b.p.113–114° C./7 mmHg.

added into the reaction column wherein were loaded 1800~3000 gm of the mixture of $SiO_2$—$Al_2O_3$ and NiO used as catalyst before above the Compound (I) warn added. And cooling the column with cyclic cooled brine to −5~15° C., at the same time turning on the revolving at agitator fitted on the top of the column and opening the valve of ammonia tank, let the liquid or gaseous ammonia flow in the column, keeping the pressure in the column at 2–5 Mpa. Under this condition, the aminolysis reaction was carrying at about 4 h. Cooling was stopped and ammonia was fed. The temperature of the reaction solution in the column rose to room temperature. The reaction was continuously stirred for 2 h. A sample from the column sent to teat. The concentration of Compound (II) should be about 10~12% in the reaction solution. The yield of Compound (II) was about 6.7~7.5 kg (yield was about 80~90%). M.P:103–104° C. IR: VNH 3330, 3260 cm$^{-1}$ IR:V$so_2$ 1355, 1600 cm$^{-1}$.

Experiment 2
Preparing p-chlorophenoxide sulfonylamide [hereafter called Compound (II)] *(Reactions proceeded in 1 liter of high-pressure reactor)

| Exp. No. | Starting Materials | | catalysts | | solvents | Pressures | Temp (° C.) | Processing time | Yield of Compd(II) | Rate of yield |
|---|---|---|---|---|---|---|---|---|---|---|
| | Compound (I) | Ammonia(I)** | Hexamethylene-amine | Metal oxide and others | | | | | | |
| 1 | 226 g(1 mol) | | 23 mg | $Al_2O_3/SiO_2$ | Benzene | 2 Mpa | −5 | 6 h | 124.2 g | 60% |
| 2 | 226 g(1 mol) | | 23 mg | NiO, $Cu_2O$ | Methylene Chloride | 3 Mpa | 0 | 6 h | 165.6 g | 80% |
| 3 | 226 g(1 mol) | | 23 mg | $Al_2O_3$/SiO NiO | Methylene Chloride | 4 Mpa | 5 | 6 h | 176.4 g | 86% |
| 4 | 226 g(1 mol) | | 23 mg | NiO, CuO Cu(OH)$NH_4$C)(OH) | Methylene Chloride | 5 Mpa | 5 | 6 h | 185.6 g | 90% |

Note:
*Operating processes as the following Exp. (5) mentioned;
**The amounts of ammonia may be calculated by pv = nRT (see the note below Experiment 1)

The 70 L of methylene chloride solution of Compound (I) (9 kg, 34 mol) and hexamethyleneamine (900 mg) were Experiment 3
Preparing 4-chloro phenyl oxide N-acetoacetylsulfamate [hereafter called Compound (III)]

| Exp. No. | Starting Materials | | catalysts | | | Temp (° C.) | Processing time | Yield of Compd(III) | Rate of yield (%) |
|---|---|---|---|---|---|---|---|---|---|
| | Compend(II) | Diketene | amine | amounts | solvents | | | | |
| 1 | 20.7 g(0.1 mol) | 9.0 g(0.1 mol) | trimethy amine | 6.0 g(0.1 mol) | acetone | 0~5 | 9.5 h | 19.8 g | 68 |
| 2 | 20.7 g(0.1 mol) | 9.0 g(0.1 mol) | Triethyl amine | 10.1 g(0.1 mol) | CH2Cl2 | −2~0 | 9.5 h | 25.3 g | 85 |
| 3 | 20.7 g(0.1 mol) | 9.0 g(0.1 mol) | Triethyl amine | 10.1 g(0.1 mol) | CH2Cl2 | 0~+2 | 9.5 h | 26.8 g | 92 |

Operating processes as the following (4) mentioned
The vessel used here was 1000 ml of two necks flask and magnetic stirrer thermometer (ibidem Experiment 2)

Compound (II) (2.8 kg 10 mol) and triethylamine (1.01 kg 10 mol) and 20L of methylene chloride was added into the 50L reactor. Stirring the suspending liquid till it became clear and cooled it to −5~0° C.

At this moment 5L of the methylenechloride solution of diketene (0.9 kg 10 mol) was added dropwise into the reactor under continuously stirring, this operation was finished within 2 h, then further stirring at the same temperature for about 1.5 h. Followed let the temperature of the reaction solution rise to the room temperature and continuously stirring for 6 h.

After this process distilled off methylene chloride, and the residue was recrystallized with methylene chloride, obtained Compound (III) about 2.35 kg, yield was about 80%. M.P: 96~98 IR: V 3185 cm$^{-1}$, Vco 1740, 1710 cm$^{-1}$ Experiment 4 preparing Acesulfame-K
Preparing Acesulfame-K was formed by cyclizing the Compound (II) dissolved in methanol with methanolic potassium hydroxide solution.

| Exp. No. | Starting Materials Compend(III) | KOH | solvents | amounts | Temp (° C.) | Processing time | Yield of Acesulfame-K | Rate of yield (%) |
|---|---|---|---|---|---|---|---|---|
| 1 | 291 g(1 mol) | 118 g(2 mol) | Ethanol | 150 ml | 0~5 | 9.5 h | 17.1 g | 85 |
| 2 | 291 g(1 mol) | 118 g(2 mol) | Methanol | 150 ml | −2~0 | 9.5 h | 18.3 g | 90 |
| 3 | 291 g(1 mol) | 118 g(2 mol) | Methanol | 150 ml | 0~+2 | 9.5 h | 18.7 g | 93 |

Operating processes as the following Exp. (4) mentioned, but the vessel used here was 500 ml of two necks flask and magnetic stirrer thermometer (ibidem Experiment 2)

After 2.9 kg (10 mols) of Compound (III) was dissolved in 10L of pure methanol then cooled the solution to 10~30° C. The reaction was stirred continuously. A solution of 11.2 kg (20 mol) of KOH in 10L methanol was steadily added dropwise within 2 h, and then at the same temperature it was continuously stirred for about 1 hour.

After finished this process, the range of PH of the solution should be about 8~10. The formed Acesulfame-K was precipitated, then filtered with suction. The by-product potassium phenoxide remains in methanol filtrate, obtained the crude Acesulfame K 2.23 kg, yield was about 80%.

First, the crude Acesulfame-K was purified with pure water, next, it was reecrystilled in distilled water for 2~3 times, last the crystal of acesulfame-K was separated with centrifugal filter. Acesulfame-K obtained by this method was conformed to the qualitative standard of FCC IV.

What is claimed is:

1. A method for preparing Acesulfame, 6-METHYL-3,4-DIHYDRO-1,2,3-OXATHIAZIN-4-ONE-2,2-DIOXIDE, comprising steps of:
   (a) using the Substituted sodium phenoxide or the substituted phenol reacted with sulfonyl chloride in a suitable inert solvent under catalysis to produce substituted phenoxide sulfonylchloride, Compound I;
   (b) reacting Compound I with ammonia under catalysts to produce substituted phenoxide sulfonyl-amide, Compound II;
   (c) reacting Compound II with diketene in an organic solvent under amine catalysts to produce Acetoacetamide-N-sulfonyl-substituted phenoxide, Compound III;
   (d) dissolving Compound III in lower alcohol and addition of alkali metal hydroxide or carbonate so that cyclization of Compound II!will occur to produce Acesulfame, 6-METHYL-3,4-DIHYDRO-1,2,3-OXATHIAZIN-4-ONE-2,2-DIOXIDE, and
   (e) isolating the produced Aceaulfame-K, Potassium salt of 6-METHYL-3,4-DIHYDRO-1,2,3-OXATHIAZIN-4-ONE-2,2-DIOXIDE.

2. The method of claim 1, wherein step (a) the inert solvent is selected from a group of alkyaryl hydrocarbons, halohydrocarbon.

3. The method of claim 2, wherein step (a) the solvent is selected from methylene chloride, 1,1-dichloroethane, and 1,2-dichloroethane.

4. The method of claim 1, wherein the catalysts is alkyl or alkoxy ammoniumhalides.

5. The method of claim 1, wherein step (a) the temperature is at approximately −10 to +20° C.

6. The method of claim 1, wherein step (a), it is stirring continuously.

7. The method of claim 1, wherein step (a), the pressure of reaction inside the column is between 2 to 10 Mpa.

8. The process in claim 1, wherein the catalysts is selected from the group consisting of following compounds: $SiO_2$—$Al_2O_3$, NiO, $Cu_2O$, $TiO_2$, $ThO_2$ and $CU(OH)NH_4$ CrOH, $NI_6Al_2C(OH)_{16}CO_3$-$4H_2O$, $Ni/Al_2O_3$—$NiO/SiO_2$, or other metals selected from: pd, pt, Ni.

9. The method of claim 1, wherein step (c), organic solvent is selected from the group consisting of benzenes, halohydrocarbon, ether, tetrahydrofuran, and acetonitrile.

10. The method of claim 1, wherein step (c), the temperature is approximately −5° C. to 10° C.

11. The method of claim 1, wherein step (c), the amine catalysts is selected from a group comprising trimethylamine, triethylamine, tri-n-propylamine, triisopropylamine, tri-n-butylamine.

12. The method of claim 1, wherein step (a) and step (b), solvents used are selected from the following organic solvent: benzene, methylenechloride monochloromethane, chloroform, ethylidene chloride, 1,2-dichloroethane, tetrahydrofuran toluene, and o-, m-, p-three kinds of xylene.

13. The method of claim 1, wherein the substituted radical R in its molecular formula, represented H—, 2-$CH_3$—, 2,6-di-$CH_3$—, 2-Cl, 4-Cl, 2-$NH_2$—, catalyst used here was selected from a group consisting of alkyl-or alkoxy-onium salts, tribenzyl ethyl ammoniumchloride, tribenzyl ammonium bromide, tetra-n-butylammonium bromide, tetra-1-butyl ammonium chloride, tetra-I-butylammonium bromide.

14. The method of claim 1, wherein step (c), the solvent is selected from the following solvent: benzene, methylenechloride, monochloromethane, chloroform, carbontetrachloride, ethylchloride, ethylidenechloride, 1, -dichloroethane, diethylether, methyl ethyl ether and tetrahydrofuran.

15. The method of claim 1, the amine catalysts are tertiary amine, in which each N atom has up to 20, or only up to 10 atoms selected as catalyst.

16. The method of claim 15, wherein the amines catalysts are trimethylamine, triethylamine, tri-n-propylamine, triisopropylamine, tri-n-butylamine, triisobutylamine, N,N-dimethylamine, or triethylamine.

17. The method of claim 1, wherein step (d), the hydroxide or carbonate of alkali metals is selected from NaOH, KON, $Na_2CO_3$, $K_2CO_3$, K alcoholate, ROK where R=$CH_3$—, $CH_3CH_2$—, $CH_3CH_2CH_2$—.

18. The method of claim 1, wherein step (d), the alcoholic solvent is a lower alkylalcohol.

19. The method of claim 18, wherein the alcohol solvent is methanol, ethanol and propanol.

20. The method of claim 1, wherein step (d), the temperature in the reaction of ring closure at approximately 10° C. to 30° C.

21. The method of claim 1, wherein step (d), the pH value at the end of the ring closure reaction was 8 to 12.

22. The method of claim 2, further comprising a cosolvent.

23. The method of claim 22, wherein the cosolvent is polyethyleneglyeol.

24. The method of claim 23, wherein the polyethyleneglyeol has M.W between 400–600.

* * * * *